United States Patent
Parker et al.

(10) Patent No.: US 6,958,372 B2
(45) Date of Patent: Oct. 25, 2005

(54) MAGNETIC, SILANISED POLYVINYLALCOHOL-BASED CARRIER MATERIALS

(75) Inventors: W. Jeffrey Parker, Halifax (CA); Jürgen Oster, Herzogenrath (DE); Lothar A Brassard, Heinsberg (DE)

(73) Assignee: Chemagen, Biopolymer-Technologie Aktiengesellschaft, Baesweiler (DE)

( * ) Notice: Subject to any disclaimer, the term of this patent is extended or adjusted under 35 U.S.C. 154(b) by 0 days.

(21) Appl. No.: 10/239,385

(22) PCT Filed: Mar. 16, 2001

(86) PCT No.: PCT/EP01/03061

§ 371 (c)(1),
(2), (4) Date: Nov. 20, 2002

(87) PCT Pub. No.: WO01/70831

PCT Pub. Date: Sep. 27, 2001

(65) Prior Publication Data

US 2003/0109618 A1 Jun. 12, 2003

(30) Foreign Application Priority Data

Mar. 22, 2000 (DE) .................................. 100 13 995

(51) Int. Cl.⁷ ............................................. C08F 120/10
(52) U.S. Cl. ......................... 525/61; 210/222; 525/62; 525/330.3; 525/342
(58) Field of Search ........................... 210/222; 525/61, 525/62, 330.3, 342

(56) References Cited

U.S. PATENT DOCUMENTS

| | | | | |
|---|---|---|---|---|
| 3,907,675 A | * | 9/1975 | Chapurlat et al. | 210/654 |
| 4,450,221 A | * | 5/1984 | Terada et al. | 430/106.2 |
| 4,628,037 A | | 12/1986 | Chagnon et al. | 436/526 |
| 4,818,624 A | | 4/1989 | Downey, Jr. | 428/447 |
| 4,822,681 A | * | 4/1989 | Schossler et al. | 428/405 |
| 5,057,426 A | * | 10/1991 | Henco et al. | 435/270 |
| 5,057,462 A | | 10/1991 | Eisenberg et al. | 437/229 |
| 5,135,832 A | * | 8/1992 | Sacripante et al. | 430/106.2 |
| 5,156,740 A | * | 10/1992 | Bruschke | 210/490 |
| 5,183,571 A | * | 2/1993 | Hanel et al. | 210/649 |
| 5,360,923 A | * | 11/1994 | Nickel et al. | 558/277 |
| 6,204,033 B1 | * | 3/2001 | Muller-Schulte | 435/181 |

FOREIGN PATENT DOCUMENTS

| | | |
|---|---|---|
| DE | 4018523 A1 | 1/1991 |
| DE | 3935098 A1 | 4/1991 |
| DE | 4139694 A1 | 6/1992 |
| DE | 4127657 A1 | 2/1993 |
| DE | 19528029 A1 | 2/1997 |
| EP | 0235526 A2 | 9/1987 |
| GB | 1439031 | 6/1976 |
| GB | 1556584 | 11/1979 |
| GB | 2267283 | 12/1993 |
| WO | WO 83/03363 | 10/1983 |
| WO | WO 96/41811 | 12/1996 |
| WO | WO 97/04862 | 2/1997 |
| WO | WO 99/17869 | 4/1999 |

OTHER PUBLICATIONS

"Development And Application Of Thermo–Sensitive Magnetic Immunomicrospheres For Antibody Purification" Kondo et al., Appl. Microbiol. Biotechnol (1994) 41:99–105.

"Preparation Of Fine Magnetic Particles And Application For Enzyme Immobilization", Shinkai et al., Biocatalysis, 1991, pp. 61–69.

* cited by examiner

*Primary Examiner*—Bernard Lipman
(74) *Attorney, Agent, or Firm*—Perman & Green, LLP

(57) ABSTRACT

The present invention relates to magnetic, polymeric polyvinylalcohol-based carrier materials. The surface of said materials is at least partially silanised. The invention also relates to a method for silanising the surface of such materials and to the use of the magnetic, silanised carrier materials for isolating biological material, preferably nucleic acids.

27 Claims, No Drawings

MAGNETIC, SILANISED POLYVINYLALCOHOL-BASED CARRIER MATERIALS

This application claims the benefit of the earlier tiled International Application No. PCT/EP01/03061, International Filing Date, 16 Mar. 2001, which designated the United States of America, and which international application was published under PCT Article 21(2) as WO Publication No. WO 01/70831 A1.

The subject of the invention is magnetic polymeric polyvinyl alcohol-based carrier materials whose surface is at least partially silanised, a method for the silanisation of the surface of such materials and the use of the magnetic, silanised carrier materials for isolating biological material, preferably for isolating nucleic acids.

Magnetic polymeric carrier materials, in particular polymer particles, are being increasingly used in biochemistry and medical diagnosis for the separation of cells, protein and nucleic acids. The use of magnetic carrier materials has the advantage over conventional separation methods that the charged carrier materials may be separated simply and quickly from the other components in a specimen with the aid of magnetic forces. Magnetic, beaded or spherical polyvinyl alcohol-based polymer particles with a narrow particle size distribution in a range below 10 $\mu$m have been found to be particularly suitable for separation processes of this kind (WO 97/04862).

It is also known that certain biological materials, in particular nucleic acids, may only be isolated from their natural environment with a greater degree of effort. This is often due to the fact that such biological samples generally contain other solid, and/or dissolved compounds, such as proteins, which could impair the isolation or due to the fact the nucleic acids are very often only present in the biological specimen to be investigated in very low concentrations.

In order, nevertheless, to exploit the advantages of the isolation of nucleic acids from biological specimens using magnetic particles it has been suggested inter alia that nucleic acids could be separated with the aid of magnetic particles with a glass surface, which is essentially non-porous (WO 96/41811). These particles must have a specific composition, i.e. their glass surface must have a specific composition, in order to achieve the desired effectiveness, in addition a relatively complex process is required to produce these particles in order to achieve the necessary sintering of the glass surface.

Therefore, it was the object of this invention to provide other magnetic carrier materials for the isolation and/or cleaning of biological materials, preferably nucleic acids from biological specimens which are preferably highly specific for nucleic acids and hence also permit automatic diagnostic processes. In addition, the production of the carrier materials must be uncomplicated and inexpensive.

According to the invention, this is achieved by the provision of polyvinyl alcohol-based magnetic carrier materials whose surface is at least partially silanised and possibly equipped with affinity ligands which couple to biomolecules.

These magnetic carrier materials may be designed as filters or membranes. Preferably, the magnetic carrier material is formed as beaded or spherical particles with these particles preferably having a particle size of 0.2 to 50 $\mu$m, particularly preferably 0.5 to 5 $\mu$m. In addition to the preferably beaded and spherical shape, their particle size distribution should be in an as narrow a range as possible.

Methods for the production of magnetic polyvinyl alcohol carrier materials, preferably with a beaded particle shape, are known from DE-41 27 657 and from WO 97/04862, the disclosure of which with regard to the production method for carrier materials is cited as a reference here. The known methods may be used to produce magnetic particles with a very narrow particle size distribution and with particle sizes of from 1 to 4 $\mu$m, such as are used in particular for the isolation of biosubstances in suspension and for diagnostic medicine.

Here, the polyvinyl alcohol particles are produced by adding specific emulsifier mixtures to the oil phase of the water in oil emulsion. Suitable emulsifiers for addition to the oil phase are propylene oxide-ethylene oxide block copolymers, sorbitan fatty acid esters, complex mixed esters from pentaerythritol fatty acid esters with citric acid, polyethylene glycol castor oil derivatives, block copolymers from castor oil derivatives, polyethylene glycols, modified polyesters, polyoxyethylene-sorbitan fatty acid esters, polyoxyethylene-polyoxypropylene-ethylenediamine block copolymers, polyglyceryl derivatives, polyoxyethylene alcohol derivatives, alkyl phenyl polyethylene glycol derivatives, polyhydroxy fatty acid polyethylene glycol block copolymers, polyethylene glycol ether derivatives. Substances of this type are known on the market inter alia under the trade names: Pluronic®, Synperonic®, Tetronic®, Triton®, Arlacel®, Span®, Tween®, BrijOR, ReneXOR, Hypermer®, Lameform®, Dehymuls® or Eumulgin®.

In order to obtain uniform beaded polymer particles, preferably with particle sizes of 0.5–10 $\mu$m, a mixture of at least two, preferably three to four of the aforesaid surface-active substances is added to the oil phase. Preferably, a lipophilic emulsifier component is mixed with at least one emulsifier with semi-hydrophilic properties, i.e. which is soluble in both water and oil. Examples of emulsifiers with the latter properties include: ethylene oxide-propylene oxide block copolymer derivatives with a predominant ethylene oxide content, polyethylene glycol hexadecylether, shorter-chain polyoxyethylene sorbitan fatty acids, polyethylene glycols or shorter chain sorbitan fatty acid esters. The concentration of the emulsifiers in the oil phase is usually 2–6 vol. %, preferably 3.5–5.0 vol. %. With reference to the fineness and narrow particle size distribution of the polymer droplets, advantageous emulsifiers are those containing at least two lipophilic components and one semi-hydrophilic emulsifier. The concentration of the semi-hydrophilic emulsifier is usually between 15 and 30 vol. % relative to the overall quantity of emulsifier. In addition to the fineness of the particle, the particles have a beaded shape.

In addition to the emulsifiers for the oil phase, special surface-active substances which are soluble in the aqueous polymer phase help to improve the emulsion quality particularly of polyvinyl alcohol solutions with a low molecular weight (Mowiol, Clariant GmbH, Frankfurt am Main, FRG). Furthermore, the addition of ionic emulsifiers achieves the fine dispersion of the magnetic colloids added in solid form. Examples of such emulsifiers, which may also be used as binary mixtures include: serum albumin, gelatins, aliphatic and aromatic sulphonic acid derivatives, polyethylene glycols, poly-N-vinylpyrrolidone or cellulose acetate butyrate. The quantities of the emulsifiers used are usually 0.01–2 wt. % relative to the polymer phase, with the concentration of the ionic emulsifiers always being between 0.01 and 0.05 wt. %. A person skilled in the art will know the influences of the stirring speeds and concentrations and viscosities of the two phases on the particle size. To achieve the preferred particle sizes of 0.5–10 $\mu$m, stirring speeds of 1500–2000 revolutions/minute are required, with conventional two-blade propeller mixers being used.

In principle, the magnetic particles which are encapsulated in the polyvinyl alcohol matrix during the process may be ferro- or superparamagnetic colloids with a suitable particle size and usually a magnetic saturation of 50–400 gauss. Another requirement which must be met by the magnetic particles is dispersibility in the aqueous polymer phase in which the polyvinyl alcohol is present. With the subsequent emulsion in the organic phase, the magnetic colloids are then simultaneously encapsulated in the polymer droplets.

Possible as magnetic colloids are preferably magnetites with particle sizes of 10–200 nm. Such substances may be obtained on the market, for example, under the trade name Bayferrox or Ferrofluidics. As the production of such colloids is known in the art, the magnetic particles may also be produced according to the known procedures, for example those described by Shinkai et al., Biocatalysis, Vol. 5, 1991, 61, Reimers and Khalafalla, Br. Patent 1,439,031 or Kondo et al., Appl. Microbiol. Biotechnol., Vol. 41, 1994, 99. Relative to this phase, the concentrations of the colloids in the polymer phase are usually between 4 and 14 vol. % for the colloids which, due to the production method, are already present as aqueous colloids and 0.3–2 wt. % for the solid substances. For the production, the magnetic colloids in the polymer are mixed in directly. In order to ensure a finely disperse, uniform distribution of the particles, the aqueous dispersion must be mixed briefly using a high-speed dispersing tool (Ultra-Turrax) followed by ultrasound treatment (sonication). The polymer phase required to produce the magnetic particles usually consists of a 2.5–10 wt. % polyvinyl alcohol solution.

The polyvinyl alcohol particles to use according to the invention should not be porous. Preferably, therefore, polymer concentrations of 2.5–5 wt. % and molar masses of >50000 g/mol should be used. Another factor associated with the porosity of the magnetic particles is the choice of crosslinking agent or its concentration. Crosslinking of the particles up to 10% obtains virtually non-porous particles. In principle, possible crosslinking agents include all water-soluble bifunctional compounds which react with the hydroxyl groups of the polyvinyl alcohol, such as, for example, aldehydes, acid chlorides or divinyl sulphone. Preferably, glutaraldehyde under acid catalysis is used as a crosslinking agent since this substance reacts with the polymers within a few minutes to form permanently crosslinked particles. With conventional substances, a reaction time of one to two hours is required. The concentrations of crosslinking agent relative to the aqueous polymer phase are usually between 0.2 and 1 vol. % and for glutaraldehyde between 2 and 7 vol. %. Glutaraldehyde is always used in the form of a 6–25% aqueous solution.

To produce the magnetic particles, generally first 20–25 times the volume quantity of an organic phase, preferably commercially available vegetable oil, is specified in which the polymer-magnetic colloid mixture is suspended under agitation.

After this, the magnetic polyvinyl alcohol carrier material may be recovered from the suspension in accordance with methods known per se to a person skilled in the art, for example by filtration and washing.

The polyvinyl alcohol-based carrier materials according to the invention are produced by converting this magnetic polyvinyl alcohol carrier material, preferably in particle form, with an organic silane compound. Particularly suitable for this conversion are silane compounds with the general formula I $$X_q\text{—Si—}(OR)_{4-q} \qquad (I)$$

where
q stands for a whole number from 0–3
R, the same or different, stands for hydrogen, an alkyl residue, preferably with $C_1$–$C_6$, particularly preferably with $C_1$–$C_2$, an aryl residue, preferably a phenyl residue
and
X, the same or different, stands for hydrogen, an alkyl residue, preferably $C_1$–$C_2$, an aryl residue, preferably a phenyl residue or a halogen, preferably chlorine
or the general formula (II), $$(Y\text{—}R^1)_q\text{—Si}(OR)_{4-q} \qquad (II)$$

where
R, q have the same meanings as given for the general formula (I)
$R^1$ stands for an alkyl residue with $C_1$–$C_6$, preferably an ethylene or propylene residue,
Y stands for an amino group, a dialkylamino group, preferably a dimethyl-diethyl amino group, SH, an epoxide group, a vinyl group, preferably a —$CR_2$=$CR^3_2$ group where $R^2$ or $R^3$, the same or different, stand for hydrogen, an alkyl residue, preferably with $C_1$–$C_2$, an aryl residue, preferably a phenyl residue or an acrylic acid residue,
or a polymer silane compound with the recurrent unit from the general formula (III)

(III)

where R has the same meaning as given for the general formula I and preferably stands for a methyl residue.

Another subject matter of the invention is a method for the repeated silanisation of the already silanised surfaces of the magnetic polyvinyl alcohol-based carrier material by conversion with organic silane compounds of the general formula II in order to introduce further functional groups which may then be converted with known affinity ligands. These affinity ligands may couple to biomolecules and be used for their isolation and identification.

In principle, all the ligands used in affinity chromatography may be coupled as affinity ligands. Examples of these which open up interesting prospects from a practical point of view include:

protein A, protein G, protein L, streptavidin, biotin, heparin, antibodies, serum albumin, gelatin, lysine, concanavalin A, oligosaccharides, oligonucleotides, polynucleotides, protein-binding metal ions, lectins or enzymes. The special separations which may be performed with such affinity matrices are general prior art. With regard to the details of this method which is known per se, reference is made to the explanations in the J. of Chromatography, Vol. 510, 1990. Usually, common to all the separations which may be performed with the aid of the surface-modified, magnetic, silanised carrier materials according to the invention is the fact that they may be performed without much effort within 2–5 minutes.

Another interesting field relating to the use of magnetic carrier materials, preferably magnetic particles, is the field of diagnostics, in particular the field of immunoassays. The underlying principle consists in the quantitative determination of specific substances. In practice, this specific binding takes place via an immobilised antibody. Here, the possibly multi-silanised magnetic carrier materials according to the invention offer an excellent basis for use for immunoassays. To do this, antibodies against specific antigens relevant to the diagnosis may be chemically bound to the magnetic particles in the known manner. Examples of such antibodies include: anti-insulin, anti-thyroxin, antibodies against the thyroid-stimulating hormone (TSH), antibodies against the thyroid-binding globulin, anti-cortisone, anti-ferritin, anti-chorionic gonadotropin, anti-carcinoembryonic antigen (CEA), anti-progesterone, anti-testosterone, anti-estradiol, anti-prolactin, anti-human growth hormone, anti-digoxin, anti-$\beta$2-microglobulin, anti-$\alpha$2-macroglobulin, anti-vitamin B12, anti-factor VIII, antibodies against cell surface antigens (so-called anti CDx antibodies) or anti-AFP. The incubation periods of the specimens with antibody-coupled magnetic carrier material is usually 2–5 minutes. After the magnetic separation of the target antigen by the formation of the highly specific, carrier-bound antibody-antigen complex, detection is performed either by using another marked antibody or by direct photometry after the detachment of the antigen under elution conditions. Besides antibodies, other substances may also be coupled to the magnetic, silanised carrier materials according to the invention, preferably in particle form, and used for the detection of specific substances. An example of such a substance is 3-amino phenyl boric acid which may be used for the detection of the blood sugar content. For the immobilisation of the ligand, it is converted with the polyvinyl alcohol carrier, whose OH-functions were activated for ligand binding with a di-isocyanate. Usually, 15–30 mg of 3-amino phenyl boric acid per 100 mg of magnetic carrier are used for the conversion. The analysis of the blood sugar content is performed using the glycosylated haemoglobin present in the blood which specifically binds to the boric acid ligands. By means of the subsequent elution of the bound glycosylated fraction from the matrix, this may be quantitatively analysed by means of photometric methods. This means that the method may be used particularly advantageously for routine analyses.

Another subject of the invention is, therefore, a method for the isolation and/or cleaning of a biological material by bringing a specimen containing biological material in a liquid, into contact with the possibly surface-modified magnetic, polyvinyl alcohol-based silanised particles according to the invention under conditions in which the biological material binds to the particle surface, and the separation of the biological material from the liquid.

As already explained, biological materials should be understood as materials with a particulate or molecular base. These include in particular cells, e.g. viruses and bacteria, and also isolated human and animal cells, such as leucocytes, and immunologically active low-molecular and high-molecular chemical compounds, such as antigens, antibodies and nucleic acids. Particularly preferred are nucleic acids, e.g. DNA or RNA, most particularly DNA, which may be selectively isolated with the polyvinyl alcohol-based silanised carrier materials according to the invention even from a very dilute solution.

Specimens within the meaning of the invention are, for example, clinical specimens, such as blood, serum, oral fluids, urine, cerebral fluid, sputum, stools, puncture fluids and bone marrow specimens. The specimen may also come from the fields of environmental analysis, food analysis or molecular-biological research, e.g. from bacterial cultures, phagolysates and products from amplification process, e.g. such as used in the PCR.

The method according to the invention may be used to isolate native or modified biological material. Native biological material should be understood as material whose structure has not been irreversibly changed compared to the naturally occurring biological materials. However, this does not exclude the modification of other components of the specimen. For example, if cells are to be isolated, although the medium surrounding the cells may be modified, the cells as such may not. If nucleic acids are to be isolated, once again these should be isolated in native form, i.e. not cut, or modified by the coupling of reactive groups. The term 'native biological material' therefore in particular does not include biotinylated nucleic acids. Examples of native biological materials include phage-DNA or cellular nucleic acids from blood.

Modified biological materials include materials which do not occur naturally in nature, e.g. nucleic acids, which have been modified by attaching groups which are reactive or detectable or which enable immobilisation, e.g. biotinylated nucleic acids.

In certain cases, the specimen may be used in the isolation process according to the invention without any pretreatment. In many cases, however, the specimen should be broken down by means of a suitable method and the biological material contained in the specimen released. Methods for the breaking down of specimens are known to people skilled in the art and may be of a chemical, enzymatic or physical nature. A combination of these materials is also possible.

Here, different methods may be more suitable for different microorganisms, but each of the methods listed below is suitable in principle:

lysis with the aid of detergents, for example, SDS, LiDS or sarkosyl in suitable buffers, the use of chaotropes, such as, for example, guanidine hydrochloride (GHCl), guanidine thiocyanate (GTC), sodium iodide (NaI), sodium perchlorate, etc., mechanical tearing apart, for example by means of a French press, ultrasound, grinding with glass beads, aluminium or in liquid nitrogen, enzymatic lysis, for example with lysozyme, proteinases, pronases or cellulases or another one of the commercially available enzymes for lysis, lysis of the cell by means of bacteriophages or virus infection, freeze-drying, osmotic shock, microwave treatment, temperature treatment, for example heating or boiling or freezing, e.g. in dry ice or liquid nitrogen and thawing, alkaline lysis.

As mentioned above, all the above-mentioned methods are standard techniques for lysis which are sufficiently well known from prior art and any of the procedures or combinations thereof may be used.

For example, a combination of chaotropes and detergents is particularly effective for bacteria cells. Therefore, an example of a suitable agent for lysis contains a chaotrope, such as GTC or GHCl for example, and a detergent, such as SDS or sarkosyl, for example. These agents for lysis may be present in an aqueous solution or in a buffer solution, i.e. as a so-called lysis buffer. Any suitable buffer may be used as a buffer, such as tris, bicine, tricine or phosphate buffers. Alternatively, the lysis agent may also be added separately. The suitable concentrations and quantities of lysis agents vary in accordance with the system in question, the type of cells, etc., and may be determined by a person skilled in the art, with, for example, it being possible to use concentrations in the range from 2M to 7M of chaotrope, such as for example, GTC, GHCl or NaI or sodium perchlorate, 0.1 M to 1 M of alkaline agents, such as NaOH or 0.1 to 50 wt. % (weight/volume) of detergents, for example. An example of a lysis buffer of this kind, therefore, contains an aqueous solution of 4 M GTC and 1% (weight/volume) of sarkosyl.

Different incubation conditions known from prior art may be suitable for different lysis systems. For example, for a lysis buffer containing detergents and/or chaotropes, incubation may be performed at room temperature or a higher temperature, for example 37 to 65° C. Equally, the incubation time may also be varied from a few minutes, for example 5 minutes, to hours, for example 1 to 2 hours. In the case of the GTC/sarkosyl lysis buffer and bacteria cells, for example, incubation at 65° C. for 10 to 20 minutes has proved satisfactory, but may also be varied if required. For enzymatic lysis, for example, using protein kinase K, etc., longer treatment times, for example overnight, may be necessary.

For the isolation of nucleic acids from biological material, in the case of modified nucleic acids, binding via the groups of nucleic acids representing the modification is possible, e.g. biotine via binding with surfaces modified with streptavidin. However, in particular with nucleic acids, the direct binding of nucleic acids to the carrier is preferred, inter alia because there is no need for modification of the nucleic acids and even native nucleic acids may be bound. In accordance with the invention, this is achieved selectively and efficiently by the use of silanised, polyvinyl alcohol-based magnetic carrier materials, even if the specimens contain the nucleic acids in a highly diluted solution and/or in a mixture with other biological materials. The binding of native nucleic acids to the carrier materials according to the invention may be performed in a similar way to the methods in prior art.

Preferably, this is performed in the presence of chaotropic salts, with the concentration of these salts being between 2 and 8 mol/l, preferably 4 to 6 mol/l. The chaotropic salts are, for example, sodium iodide, sodium perchlorate, guanidinium thiocyanate, guanidinium isothiocyanate or guanidininium hydrochloride. However, the binding is not restricted to these compounds.

For isolation, the specimen is brought into contact with the carrier material, preferably the particles, and incubated for a time sufficient for the binding. For nucleic acids, incubation times of between 10 seconds and 30 minutes may be expedient.

For the isolation of nucleic acids, preferably silanised, magnetic particles are used which have a beaded or spherical shape and a particle size in the range of 0.2 to 50 $\mu$m, preferably 0.5 to 5 $\mu$m, with a very narrow size distribution.

The incubation is followed by the separation of the biological material, preferably the nucleic acids, from the specimen liquid. This is in general achieved by separating the nucleic acids bound to the magnetic particles according to the invention with assistance of a magnetic field. For example, the magnetic particles may be pulled on the wall of the vessel in which the incubation took place. Following this, the liquid may be removed with the contents of the specimen which were not bound to the magnetic particles. This removal depends upon the type of vessel in which the incubation took place. Suitable steps for the removal of the liquid are, for example, the pipetting-off or siphoning-off of the liquid.

Since the magnetic, silanised carrier material very selectively binds nucleic acids from biological specimens without any contamination of the carrier material with other biological materials occurring, the washing stages may be significantly reduced.

If desired, the charged magnetic particles may be cleaned once or several times with a washing solution. The washing solution is selected to ensure that if possible no detachment of the biological material, e.g. the nucleic acids, from the particle surface takes place, but that any contaminants are washed away as well as possible. This washing stage is preferably performed by incubating the washing solution with the charged particles, with preferably a resuspension of the particles being performed, for example by shaking or applying a magnetic field which is not identical to the first magnetic field. The contaminated washing solution is preferably removed in exactly the same way as the specimen liquid remaining after the isolation of the nucleic acids.

Any conventional washing buffer or any other suitable medium may be used as the washing solution. Generally, buffers with a low to moderate ionic strength are preferred, such as for example 10 mM tris-HCl at pH 8.0/10 mM NaCl. Other standard media for washing, e.g. media containing alcohol may also be used, such as 70% ethanol, for example.

The use of magnetic particles permits simple washing stages simply by the magnetic aggregation of the particles, the removal of the nucleic acid binding medium, the addition of the washing medium and the re-aggregation of the particles as often as required.

Following the method for nucleic acid isolation and each washing stage desired, if applicable, the carrier carrying the nucleic acid may be transferred to any suitable medium, e.g. water or a buffer with a low ionic strength, for example resuspended or immersed.

Following the last washing stage, a short drying stage for the magnetic particles may be performed in a vacuum or by (permitting) the evaporation of the liquid, with pretreatment with acetone also being possible. A person skilled in the art will understand that the above-described washing and drying stages may be performed not only during the cleaning and/or isolation of nucleic acids, but also for the cleaning and/or isolation of the other aforesaid biological materials.

Depending upon the carrier and the nature of the subsequent processing, it may be desirable to detach the nucleic acids from the carrier or not to detach them from the carrier. In the case of a particularly solid carrier, such as the magnetic particles according to the invention, in many cases it may be used directly, such as for example in the PCR or other amplification methods without the nucleic acids having to be eluted from the carrier. In addition, elution is also not required for numerous DNA detection methods or identification methods, since although the DNA fortuitously comes into contact with the surface of the spheres and may be bound at numerous points by hydrogen bridging bonds or ionic bonds or other forces, there is a sufficient length of DNA for hybridisation with oligonucleotides and for multiplication.

In the event of the biological material consisting of native nucleic acids, the nucleic acid may be removed from the particles according to the invention by means of an elution buffer with a low salt content. Buffers of this kind are known from Analytical Biochemistry 175, 196–201 (1988). Used as elution buffers with a low salt content are in particular buffers with a salt content of less than 0.1 mol/l. Particularly preferably, the elution buffer contains tris HCl. Also particularly suitable is demineralised water.

If desired, it is also possible to remove the RNA from the DNA, which could also be achieved by the destruction of the RNA before the DNA separation stage, for example, by the addition of RNAse or an alkali, such as NaOH, for example.

Another subject of the invention is the cleaning and/or isolation of nucleic acids, preferably DNA, by the use of the possibly surface-modified, silanised, magnetic carrier materials according to the invention.

Another subject of the invention is kits containing the carrier materials according to the invention, preferably in the form of beaded or spherical, finely dispersed particles and solutions suitable for the isolation of nucleic acids, preferably from biological specimens.

The method according to the invention for the isolation of nucleic acids may also be performed subsequent to an immunomagnetic separation of cells from a bodily fluid or a tissue. For this, the specimen with the above-described magnetic particles according to the invention, on which an antibody against an antigen is immobilised on the cell, may be incubated, for example with shaking. After the application of a magnetic field, one or more washing stages are performed with a saline washing solution. In this way, particles are obtained to which the desired cells are bound. Finally, the bound cells are resuspended in a saline buffer. In a preferred embodiment, this saline buffer is a chaotropic salt solution, so the nucleic acids are released from the cell.

The combination of the above-described isolation of cells according to the invention with the also described isolation of nucleic acids in accordance with the invention, preferably in their native form on the magnetic carrier materials according to the invention, preferably in particle form, achieves a particularly advantageous method for the isolation of nucleic acids from specimens containing cells. The advantage of this embodiment is its simplicity, high sensitivity and selectivity and the ease of automation.

The biological materials isolated as a result of the method according to the invention may now be further used as desired. For example, they may be used as a substrate for different enzymatic reactions. In the case of nucleic acids, examples cited are sequencing, radioactive or non-radioactive marking, the amplification of one or more of the sequences contained therein, transcription, hybridisation with marked special nucleic acids, translation or ligation. One advantage of the method according to the invention is that the separation of the biological material, in particular the nucleic acids, from the liquid is very simple.

The invention will be further described in the following with reference to examples, which do not, however, restrict the general inventive concept.

EXAMPLE 1

1a) Silanisation 55 mg of supraparamagnetic polyvinyl alcohol particles with a particle size of 0.5 to 1 $\mu$m were suspended in 2.5 ml of an aqueous solution of sodium acetate (concentration 100 mM, pH=5.5) in a reaction vessel and heated in an oil bath to a temperature of 90° C. Then, 25 $\mu$l of tetramethoxysilane (Fluka, Deisenhofen) were added to the reaction vessel and the reaction mixture incubated for 2 hours with agitation. After the expiry of the two hours, the magnetic carrier material was washed three times with 30 ml of distilled water in each case and resuspended in water.

1b) Isolation of DNA:

The isolation of 1 $\mu$g of native lambda DNA (Fischer Biotech, Nidderau) was performed using 50 $\mu$g of particles silanised according to example 1a).

50 $\mu$g of the particles were suspended in 250 $\mu$l of 7M NaClO$_4$. The suspension obtained in this way was then added to a microlitre vessel with 1 $\mu$g lambda DNA in 100 $\mu$l of water. Then, the content of this vessel was mixed and incubated for 5 minutes at room temperature. Following the incubation, the particles were separated with the aid of a magnetic separator (chemagen AG, Baesweiler, FRG). The supernatant was discarded and the particles were washed three times in 500 $\mu$l of a 70% ethanol washing solution in each case, with the particles being magnetically separated after every washing process and the supernatant being discarded. Following the last washing process, the particles were dried for 5 minutes in air.

Then, the particles were resuspended in the reaction vessel in 35 $\mu$l of a 10 mM triaminomethane hydrochloride (tris-HCl) solution (pH 8.0) and incubated at a temperature of 55° C. on a water bath for 10 minutes with occasional shaking. Then, the particles were separated from the supernatant and the supernatant transferred to a clean microlitre vessel.

15 $\mu$l of the eluate were then loaded on to a stained 1.5% agarose gel (Gelstar®, FMC Corporation). Electrophoresis was then performed using TBE buffer (0.1 M, pH 8.4, Life Technologies, Karlsruhe).

The evaluation of the gel electrophoresis revealed a strong, clearly detectable signal for the DNA isolated with the aid of the silanised magnetic carrier materials according to the invention.

EXAMPLE 2

Comparative Example

Isolation of DNA:

The isolation of 1 $\mu$g of native lambda DNA (Fischer Biotech, Nidderau) was performed using 50 $\mu$g of the magnetic polyvinyl alcohol particles according to example 1a), which had not been silanised.

50 $\mu$g of the particles were suspended in 250 $\mu$l of 7M NaClO$_4$. The suspension obtained in this way was then added to a microlitre vessel with 1 $\mu$g lambda DNA in 100 $\mu$l of water. The content of this vessel was then mixed and incubated for 5 minutes at room temperature. After the incubation, the particles were separated from the solution by means of a magnetic separator (chemagen AG, Baesweiler, FRG). The supernatant was discarded and the particles were washed three times with 500 $\mu$l of a 70% ethanol washing solution in each case, with the particles being magnetically separated after every washing process and the supernatant being discarded. Following the last washing process, the particles were dried for 5 minutes in the air.

The particles then resuspended in the reaction vessel in 35 $\mu$l of a 10 mM tris HCl solution (pH 8.0) and incubated at a temperature of 55° C. on a water bath for 10 minutes with occasional shaking. Finally, the particles were separated from the supernatant in the magnetic separator and the supernatant transferred to a clean microlitre vessel.

15 $\mu$l of the eluate were then loaded on to a stained 1.5% agarose gel (Gelstar®, FMC Corporation). Electrophoresis was then performed using TBE buffer (0.1 M, pH 8.4, Life Technologies, Karlsruhe).

The evaluation of the gel electrophoresis revealed a weak, scarcely detectable signal for the DNA isolated with the aid of the unsilanised carrier materials.

EXAMPLE 3

2 $\mu$l of proteinase K (20 mg/ml in water, Appligene, Heidelberg) and then 100 $\mu$l of lysis buffer (1 M guanidinium hydrochloride, 10 mM tris-HCL, 6% Triton X-100, pH 7) were added to 10 $\mu$l of human whole blood treated with ethylene diamine tetra acetic acid (EDTA). The mixture was incubated for 15 minutes at 45° C. and then added to 600 $\mu$g of the silanised magnetic particles in accordance with example 1a) and 300 $\mu$l of binding buffer (90% ethanol, 100 mM tris HCL, pH 7). After 10 minutes incubation of the previously well mixed suspension at room temperature, the magnetic particles were separated magnetically in a magnetic separator (chemagen AG, Baesweiler, FRG) and the supernatant discarded. The DNA bound to the particles was washed three times with 1 ml of 80% isopropanol in each case and then dried for 10 minutes in the air in order to remove any residual isopropanol. It was resuspended in 30 $\mu$l of TBE buffer and incubated for 10 minutes at 65° C. After magnetic separation, the eluted DNA solution was separated and the DNA subjected to amplification using PCR technology.

EXAMPLE 4
Isolation of Genomic DNA From 5 ml of Whole Blood 5 ml of whole blood (EDTA-stabilised) were mixed in a 50 ml reaction vessel with 6.25 ml of lysis buffer (1.2 M guanidine hydrochloride, 30 mM tris HCl, pH 7, 30 mM EDTA, 10% Tween 20® and 1% Triton X-100® from Fluca) and incubated for 5 minutes at room temperature. Then, 600 μl of the modified particles from example 1 and 18 ml of binding buffer (60% ethanol, 1.2 M NaClO$_4$, 0.2 M sodium acetate) were added. After five minutes incubation at room temperature, the supernatant was discarded after magnetic separation. The particles were then washed with 30 ml of washing buffer A (30% ethanol, 1.1 M NaClO$_4$, 0.15 M sodium acetate), then washed twice in 30 ml of 60% ethanol in each case and then briefly washed with 40 ml of water. After the separation of the last washing solution, elution was performed in 1 ml of 10 mM tris HCl by means of five minutes' incubation at 55° C. The isolated genomic DNA may be used directly, e.g. in a PCR.

EXAMPLE 5
Cleaning a PCR Amplification Product

A 595 bp DNA fragment of the malB region of genomic DNA isolated from *E. coli* bacteria (K12) with the aid of a kit comprising magnetic polyvinyl alcohol-based particles binding bacteria and bacterial DNA, the so-called Bugs'n Beads Kit (M-PVA DNA 200 Kit from chemagen AG) was amplified in a PCR (primer and condition corresponding to Candrian et al. Int. J. Food Microbiol. 12 (1991) 339). 50 μl of the PCR product were mixed with 16 μl of the particle suspension from example 1 and 100 μl of binding buffer (90% ethanol, 100 mM tris HCl, pH 7). After five minutes' incubation, it was magnetically separated and the supernatant discarded. It was washed twice with 400 μl of 60% ethanol in each case and the particles, after the complete separation of the washing solution, dried for 8 minutes in an open vessel. Then, it was resuspended in 30 μl of 10 mM tris HCl pH 8.0 and after 5 minutes' incubation at 55° C., the supernatant and the cleaned DNA amplificate separated from the magnetic particles and transferred to a new vessel.

EXAMPLE 6
Isolation of Plasmid DNA From *E-coli* Bacteria 1.5 ml of bacteria culture (*E. coli* with plasmid pUC18, overnight culture) were first centrifuged in a 1.5 ml reaction vessel at 6000 g for two minutes and the supernatant discarded. The bacteria pellet was resuspended with 100 μl of resuspension buffer (TE buffer, pH 8), 100 μl of lysis buffer (0.1 M NaOH, 0.2% of sodium dodecyl sulphate (SDS)) was added and incubation was performed for 5 minutes at room temperature. Then, 140 μl of neutralisation buffer (4 M guanidine hydrochloride, 0.5 M potassium acetate, pH 4.2) and 20 μl of the modified particles from example 1 were added. After five minutes' incubation at room temperature, the supernatant was discarded after magnetic separation. Then, the particles were washed with 500 μl of washing buffer A (30% ethanol, 1.1 M NaClO$_4$, 0.15 M sodium acetate) and then washed with 500 μl of 70% ethanol. After the separation of the last washing solution, the particles were dried in the air for 6 minutes and eluted in 50 μl 10 mM tris HCl by means of five minutes' incubation at 55° C.

EXAMPLE 7
Isolation of Viral DNA (From Hepatitis B Viruses, HBV) From Serums 200 μl of serum from a hepatitis B positive patient were intermixed in a 1.5 ml reaction vessel with 200 μl of lysis buffer (1.2 M guanidine hydrochloride, 30 mM tris HCl, 30 mM EDTA, 10% Tween 20 and 1% Triton X-100) and incubated for 5 minutes at room temperature. Then, 30 μl of the modified particles from example 1 and 600 μl of binding buffer (60% ethanol, 1.2 M NaClO$_4$, 0.2 M sodium acetate) were added. After five minutes' incubation at room temperature, the supernatant was discarded after magnetic separation. The particles were then washed with 500 μl of washing buffer A (30% ethanol, 1.1 M NaClO$_4$, 0.15 M sodium acetate) and then washed with 500 μl of 70% ethanol and then briefly with 600 μl of water. After separation of the last washing solution, elution was performed in 1 ml 10 mM of tris HCl by means of five minutes' incubation at 55° C. The isolated viral DNA may be used directly, e.g. in the PCR, with specific primers for the diagnosis of the hepatitis B virus.

What is claimed is:

1. Magnetic polyvinyl alcohol carrier materials whose surface is at least partially silanised and optionally equipped with affinity ligands which couple to biomolecules.

2. Polyvinyl alcohol carrier material according to claim 1 characterised in that it is ferromagnetic or superparamagnetic.

3. Polyvinyl alcohol carrier material according to claim 1 characterised in that it is present in the form of hydrogel.

4. Polyvinyl alcohol carrier material according to claim 1 characterised in that it is present in the form of beaded or spherical particles.

5. Polyvinyl alcohol carrier material according to claim 4 characterised in that particles have a particle size of 0.2 to 50 μm.

6. Polyvinyl alcohol carrier materials according to claim 1 characterised in that it is present in the form of filters or membranes.

7. Method for the production of a surface-modified, magnetic polyvinyl alcohol carrier material according to claim 4 characterised in that the polyvinyl alcohol carrier material is converted with an organic silane compound.

8. Method according to claim 7 characterised in that the silane compound used is at least one silane compound with the general formula (I)

$$X_q\text{—Si—(OR)}4\text{-q} \qquad (I)$$

where q is a whole number from 0–3

R, the same or different, stands for water, an alkyl residue, preferably with C1–C6, particularly preferably with C1–C2, an aryl residue, preferably a phenyl residue and X, the same or different, stands for hydrogen, an alkyl residue, preferably C1–C2, an aryl residue, preferably a phenyl residue or a halogen, preferably chlorine, or the general formula (II)

$$(Y\text{—R1})q\text{—Si(OR)}4\text{-q} \qquad (II)$$

where

R, q have the same meanings as given for the general formula (I)

R1 stands for an alkyl residue with C1–C6, preferably an ethylene or propylene residue, Y stands for an amino group, a dialkylamino group, preferably a dimethyl-diethyl amino group, SH, an epoxy group, a vinyl group, preferably a —CR2=CR32 group where R2 or R3, the same or different, stand for hydrogen, an alkyl residue, preferably with C1–C2, an aryl residue, preferably a phenyl residue or an acrylic acid residue, or a polymer silane compound with the recurrent unit from the general formula (III)

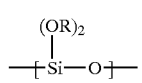
(III)

where R has the same meaning as given for the general formula I and preferably stands for a methyl residue.

9. Method according to claim 7 characterised in that the conversion is performed at temperatures of from 70 to 150° C., preferably from 80 to 100° C.

10. Method according to claim 7 characterised in that the polyvinyl alcohol particles are suspended for conversion in an aqueous medium preferably with a pH or 2 to 7.

11. Method according to claim 7 characterised in that the polyvinyl alcohol particles are suspended in a hydrophobic, organic solvent for conversion.

12. Method according to claim 7 characterised in that the conversion is performed with intermixing of the polyvinyl alcohol carrier material and the silane compound, and for a duration of from 1 minute to 48 hours.

13. Method according to claim 7 characterised in that OH groups on the surface of the polyvinyl alcohol carrier material are converted with a 1.2 to 1.8 equivalent quantity of the silane compounds.

14. Method according to claim 8 characterised in that after conversion with the at least one silane compound of the general formulas I to III, the polyvinyl alcohol carrier material, possibly after separation from the reaction medium and cleaning, is converted again with a silane compound with the general formula II.

15. Method according to claim 7 characterised in that the silanised polyvinyl alcohol carrier material is converted with affinity ligands which couple to biomolecules.

16. Column filling for chromatographic separation consisting of polyvinyl alcohol carrier material according to claim 4.

17. Method for the isolation of biological material characterised in that polyvinyl alcohol carrier material magnetic particles, obtainable according to claim 15, are used for the immobilisation and separation of the biological material.

18. Method for the isolation and/or cleaning of nucleic acids from a biological specimen characterised in that polyvinyl alcohol carrier material magnetic particles according to claim 1 are used for the immobilisation and separation of the nucleic acids.

19. Method according to claim 18 characterised in that the biological specimen is mixed with a buffer solution suitable for extraction of nucleic acids.

20. Method according to claim 19 characterised in that before the extraction, the biological specimen is mixed with an agent, the agent being at least one of RNAse or an alkali which destroys the ribonucleic acid (RNA).

21. A kit for isolation of deoxyribonucleic acids comprising a polyvinyl alcohol carrier material according to claim 1, a solution for the destruction of ribonucleic acids and a solution for the extraction of the deoxyribonucleic acid.

22. A kit for isolation of nucleic acids comprising a polyvinyl alcohol carrier material according to claim 1 and a solution for the extraction of the nucleic acids.

23. Column filling for chromatographic separation from polyvinyl alcohol particles obtainable according to the method of claim 7.

24. Method for the isolation and/or cleaning of nucleic acids from a biological specimen characterised in that polyvinyl alcohol carrier material magnetic particles obtainable according to claim 7 are used for the immobilisation and separation of the nucleic acids.

25. A kit for isolation of deoxyribonucleic acids comprising a polyvinyl alcohol carrier material obtainable according to claim 7, a solution for the destruction of ribonucleic acids and a solution for the extraction of the deoxyribonucleic acid.

26. A kit for isolation of nucleic acids comprising a polyvinyl alcohol carrier material obtainable according to claim 7 and a solution for the extraction of the nucleic acids.

27. Polyvinyl alcohol carrier material according to claim 5 wherein the particles have a particle size of 0.5 to 5 μm.

* * * * *